United States Patent [19]

Nowak, Jr. et al.

[11] 4,009,256

[45] Feb. 22, 1977

[54] NOVEL SHAMPOO COMPOSITION CONTAINING A WATER-SOLUBLE CATIONIC POLYMER

[75] Inventors: Frank A. Nowak, Jr., Bound Brook; Albert L. Micchelli, Middletown; Gerard J. Legato, Stirling, all of N.J.

[73] Assignee: National Starch and Chemical Corporation, Bridgewater, N.J.

[22] Filed: Nov. 13, 1975

[21] Appl. No.: 631,519

Related U.S. Application Data

[63] Continuation-in-part of Ser. No. 417,260, Nov. 19, 1973, abandoned.

[52] U.S. Cl. .................... 424/70; 252/542; 252/545; 252/546; 252/547; 252/DIG. 2; 252/DIG. 3; 252/DIG. 13; 424/DIG. 2; 424/71; 424/81
[51] Int. Cl.$^2$ ................................ A61K 7/06
[58] Field of Search ............... 424/DIG. 2, 70, 71, 424/81; 252/542, 545, 546, 547

[56] References Cited

UNITED STATES PATENTS

| | | | |
|---|---|---|---|
| 2,138,763 | 11/1938 | Graves | 260/89.7 N |
| 2,694,688 | 11/1954 | Hughes | 260/89.7 N X |
| 2,808,349 | 10/1957 | Melamed | 260/89.7 N X |
| 2,979,491 | 4/1961 | Piloni | 260/89.7 N X |
| 3,239,496 | 3/1966 | Jursich | 260/89.7 N X |
| 3,313,734 | 4/1967 | Lang et al. | 424/70 X |
| 3,361,718 | 1/1968 | Fujimoto et al. | 260/89.7 N X |
| 3,372,149 | 3/1968 | Fertig et al. | 260/78.4 |
| 3,580,853 | 5/1971 | Parran | 424/70 X |
| 3,642,977 | 2/1972 | Hewitt | 424/70 |

*Primary Examiner*—Albert T. Meyers
*Assistant Examiner*—Vera C. Clarke

[57] ABSTRACT

A shampoo composition is disclosed comprising an aqueous solution of (1.) a cationic polymer which is a water-soluble acid salt of an aminoalkyl ester of a carboxylic acid polymer, (2.) an amphoteric detergent, and, (3.) optionally, at least one nonionic surfactant or at least one ionic surfactant or a combination thereof, wherein any plurality of ionic surfactants utilized consists of those of the same ionogenic class.

5 Claims, No Drawings

NOVEL SHAMPOO COMPOSITION CONTAINING A WATER-SOLUBLE CATIONIC POLYMER

This application is a continuation-in-part of U.S. Ser. No. 417,260, filed Nov. 19, 1973, now abandoned.

This invention relates to a novel shampoo composition capable of imparting to the hair unusual conditioning properties normally expected of a creme rinse or a conditioner as well as cleaning the hair. More particularly, this invention relates to a shampoo composition comprising an aqueous solution of an acid salt of a cationic polymer and an amphoteric detergent.

It is well known that subtantial quantities of natural oil are removed from the hair during shampooing and that such loss, due to the repeated washing and rinsing, adversely affects the quality of the hair. For example, upon rinsing, the hair loses body, becomes brittle, and ultimately less manageable. That is to say, because of the decrease in natural oil, it becomes extremely difficult to set the hair in a desired configuration, unless a commercial application designed for that purpose is subsequently used.

It is also well known that many commercial applications which are intended as means to compensate for the abovementioned inherent drawbacks of conventional shampoo compositions are readily available. These products, commonly referred to as creme rinses or spray conditioners, generally form a film on the hair fibers thereby improving the condition of the hair. Since use of these products normally calls for a multi-step procedure subsequent to shampooing, there exists a need for a shampoo composition, which when employed in the conventional manner, is capable of rendering the hair more manageable and otherwise improving the condition of the hair. Hence it becomes obvious that any combination hair washing and conditioning substance must meet a number of rigid requirements normally expected of a conventional shampoo composition and, to an appreciable extent, those of a conditioner, when the latter two are used, separately.

In order to be effective in a shampoo composition, a conditioning agent must be capable of functioning adequately, as well as exhibiting the desired compatibility with any other ingredient without detracting from the overall performance of the shampoo composition. Thus, a conditioning agent must be capable of depositing a film on the hair, which displays good adhesion thereto so as to avoid dusting and flaking off with the passage of time or when the hair is subjected to stresses; it should not interfere with the combing and brushing of the hair; it should remain free of tackiness or gumminess under humid conditions; it should be clear, transparent, and glossy, and capable of maintaining clarity upon aging; it should maintain good antistatic properties; and it should be easily removable by washing with water and either soap or shampoo.

Heretofore various natural and synthetic conditioning agents, e.g., waxes, polyglycols and their fatty acid esters, lanolin derivatives, etc., have been incorporated into conventional shampoo formulations. But, these and other material proposed as conditioning agents have been of limited usefulness, due to undesired characteristics such as low electrochemical bonding ability with resulting poor affinity for the hair fibers, low molecular weight which causes emulsification and undesired rinsing away; and oiliness which inhibits lathering.

It is thus an object of this invention to provide shampoo compositions which not only cleanse hair but also improve its condition. It is a further object of this invention to provide shampoo compositions having a conditioning agent capable of imparting excellent combing properties to the washed hair without incurring any of the inherent drawbacks of the conditioning agents mentioned above.

These and various other objects and advantages of this invention will become apparent to the practitioner from the following detailed description thereof.

We have now discovered that all of the previously described functions of a multi-step washing and conditioning sequence are met by utilizing a shampoo composition comprising an aqueous solution of (1) from 0.1 to 10.0 percent, by weight of the total solution, of a water-soluble acid salt of an aminoalkyl ester of a carboxylic acid polymer having a molecular weight of 5,000 to 250,000; (2) from 1 to 25 percent, by weight of the total solution, of an amphoteric detergent; and (3) from 0 to 20 percent, by weight of the total solution, of at least one surfactant selected from the group consisting of nonionic surfactants, ionic surfactants and combinations thereof other than the amphoteric detergents of part (2) wherein any plurality of ionic surfactants utilized consists of those of the same ionogenic class. When used as a shampoo the composition deposits the cationic polymer on the hair fibers. During rinsing, the polymer precipitates as a microscopically thin layer which when dried, encases the hair filaments thereby improving hair condition. For example, combability manageability and wave retention properties of the dried hair are improved. The novel shampoo compositions herein display excellent cleaning and conditioning characteristics, when employed in a conventional manner.

The shampooing process, using the shampoo compositions of this invention, comprises the steps of applying to the wet hair a preparation of this invention as already described; massaging the shampoo bearing hair until the lather thus produced is uniformly distributed throughout the hair fibers; thoroughly rinsing the lather from the hair with water; partially drying the hair; combing it out; and allowing it to dry while held in a desired configuration.

As previously mentioned, the novel shampoo compositions of this invention comprise aqueous solutions of (1.) a resin depositing, cationic polymer in the form of an acid salt of a non-quaternized aminoalkyl ester of a polymer of unsaturated carboxylic acids or derivatives of said acids, (2.) a portion which consists of an amphoteric detergent, and (3.) at times, an additional surfactant portion comprising one or more nonionic or ionic surfactants or a combination thereof, wherein any plurality used is void of an anionic and cationic mixture.

The novel, hair conditoning shampoo compositions of this invention are prepared by dispersing the resin depositing, cationic polymer and the amphoteric detergent in water with moderate agitation. When a homogeneous system of these two ingredients in the water is obtained, any optional ingredients may be added under appropriate conditions. For instance, the addition of a compound such as an amide may require heating the solution to ensure dispersion of the melted waxy material and the subsequent addition of a particular compound such as a perfume will require adequate cooling, prior thereto, to avoid its volatilization. Also, it may be desired to slightly adjust the pH level.

The pH adjusting agent and quantity to be used should be chosen to ensure maximum efficiency of a shampoo composition which will not damage the hair or irritate the eyes or skin. A preferred pH range, for the solutions prepared according to this invention, is from 3.5–7.0. Since the initial pH level of the shampoo compositions herein is usually between 5.0 and 6.0, it is preferred that weak acids such as citric acid acetic acid, phosphoric acid, and the like and weak bases such as the alkanolamines, e.g., triethanolamine, diethanolamine, etc. be used as pH adjusting agents.

Among the various cationic polymers useful in the practice of this invention are included the mineral acid salts of the amino-alkyl esters of homo- and copolymers of unsaturated carboxylic acids having from 3 to 5 carbon atoms, for example, acrylic acid, methacrylic acid, crotonic acid, ethacrylic acid, fumaric acid, maleic acid and itaconic acid, and the aminoalkyl groups containing from 2 to 6 carbon atoms. Useful aminoalkyl groups include, for example, aminoethyl, N-methyl aminoethyl, N-ethyl aminoethyl, 2-aminopropyl and t-butyl aminoethyl, with the aminoethyl being preferred.

More specifically, the useful polymers include the salts of the aminoalkyl esters of (a) homopolymers of homopolymerizable unsaturated carboxylic acids having 3 to 5 carbon atoms; (b) copolymers of copolymerizable mixtures of said acids, and (c) copolymers formed of unsaturated carboxylic acids having 3 to 5 carbon atoms and at least one copolymerizable ethylenically unsaturated comonomer selected from the group consisting of vinyl acetate and vinyl propionate; vinyl methyl ether and vinyl ethyl ether; the $C_1$-$C_8$ alkyl half esters of maleic and fumaric acids, for example, diethyl fumarate, dioctyl fumarate, dibutyl maleate, dioctyl maleate, monobutyl maleate, monomethyl fumarate, and monooctyl fumarate; amides of acrylic and methacrylic acids, for example, acrylamide, N-methyl acrylamide, and methacrylamide; and the $C_1$-$C_{18}$ alkyl and $C_2$-$C_4$ hydroxyalkyl esters of acrylic and methacrylic acids. Specific examples of the latter class of comonomers includes methyl acrylate, ethyl acrylate, butyl acrylate, octyl acrylate, dodecyl acrylate, stearyl acrylate, hydroxyethyl acrylate, hydroxypropyl acrylate, as well as the corresponding methacrylate esters. Preferred comonomers include the amides and the $C_1$-$C_{18}$ alkyl and $C_2$-$C_4$ hydroxyalkyl esters of acrylic and methacrylic acids.

It will be recognized that, for the purposes of the present invention, the copolymeric mixture of copolymerizable carboxylic acids of group (b) may contain the various monomeric components in any proportion. However, in the case of the copolymers of group (c), there must be present at least 50 mole percent, and preferably 75 mole percent, of the unsaturated carboxylic acid component.

With regard to the preparation of cationic polymers useful in the practice of this invention, the practitioner will recognize that such materials may be commercially available or may normally be synthesized either (1.) by polymerizing monomers which have the functional aminoalkyl ester groups attached or (2) by subsequently affixing said groups to a base polymer such as the homopolymer of an ethylenically unsaturated carboxylic acid or a copolymer formed with at least one ethylenically unsaturated carboxylic acid and one or more copolymerizable comonomers. For example, the first method would typically involve the homopolymerization of one of the following: t-butylaminoethyl methacrylate, dimethylaminoethyl methacrylate, or the copolymerization of any one of the foregoing compounds with one or more of the above-mentioned copolymerizable comonomers. Such methods are disclosed in, inter/alia, Piloni, U.S. Pat. No. 2,979,491; P. L. deBenneville, U.S. Pat. No. 2,744,884; and in Mowry et al., U.S. Pat. No. 2,625,471. The second method wherein the functional aminoalkyl ester groups are affixed to the base polymer may be carried out according to the process taught in, inter alia, assignee's Fertig et al. U.S. Pat. No. 3,372,149, the disclosure of which is incorporated herein by reference. Regardless of the means of synthesis selected, a wel-known free radical polymerization procedure is usually entailed. These compounds, upon utilization in accordance with this invention, are all characterized by their ability to display the desirable hair conditioning properties.

The amphoteric detergents useful in the practice of this invention include any of the following classes: the alkali metal salts of the long chain alkyl ($C_8$-$C_{18}$) imidazoline derivatives having either one or two carboxylic acid groups substituted on the nitrogen atom in the 1 position of the imidazolidyl ring; the higher alkyl and higher alkyl amino alkyl substituted betaines wherein said higher alkyl groups contain from 8–18 carbon atoms; the long chain ($C_8$-$C_{18}$) amino sulfonates; the sulfonated alkyl amides, wherein said alkyl groups contain from 8–18 carbon atoms, and the N-alkyl-beta-amino propionic acids, wherein the alkyl group contains 8–18 carbon atoms. Such compounds are compatible with both anionic and cationic surfactants. The useful compounds of each of the aforementioned general classification are more specifically described below.

Suitable long chain monocarboxylic imidazoline derivatives of the type mentioned above are those compounds corresponding to the following general structure:

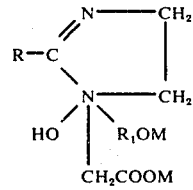

wherein R represents an alkyl radical having from 8–18 carbon atoms, M represents a cation salt forming group such as an alkali metal, e.g., sodium, potassium, lithium, etc., or hydrogen, and $R_1$ is a bivalent lower alkyl group having from 2–4 carbon atoms. Examples of such compounds are the monocarboxylate coconut imidazoline derivative sodium salt, the monocarboxylate caprylic imidazoline derivative sodium salt, the monocarboxylate capric imidazoline derivative sodium salt, the monocarboxylate lauric imidazoline derivative sodium salt, the monocarboxylic stearyl imidazoline derivative sodium salt, the monocarboxylate oleic imidazoline derivative sodium salt, etc.

Suitable long chain dicarboxylic imidazoline derivatives of the type mentioned above are those compounds corresponding to the following general structure:

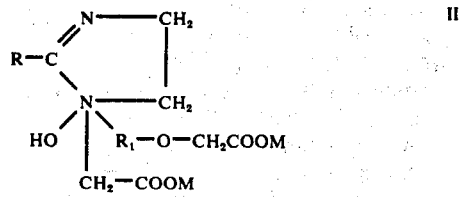

II wherein R, $R_1$, and M are as defined above in structure I. Examples of such compounds are the dicarboxylate caprylic imidazoline derivative sodium salt, the dicarboxylate capric imidazoline derivative sodium salt, the dicarboxylate lauric imidazoline derivative sodium salt, the dicarboxylate coconut imidazoline derivative sodium salt, the dicarboxylate oleic imidazoline derivative sodium salt, the dicarboxylate stearyl imidazoline derivative sodium salt, and the like.

Generally, such compounds are commercially available. Also they may be synthesized using well-known methods as discussed by Schwartz et al. in "Surface Active Agents and Detergents," II (1958) 141–142. Additional information concerning these compounds may be obtained by reference to, inter alia, Mannheimer U.S. Pat. Nos. 2,528,378 and 2,773,068.

Included among the substituted betaines useful in the novel shampoo compositions herein are the internal salts of the trialkyl carboxy alkyl and dialkyl, amido alkyl carboxy ammonium hydroxide which corresponding to the following general structure.

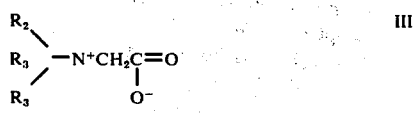

III wherein $R_2$, is one of the following: an alkyl group having from 8–18 carbon atoms; an amido group having from 8–18 carbon atoms in the chain; an alkyl group having 8–18 carbon atoms which may contain one or more intermediate linkages, e.g. ether or ester linkages, or nonfunctional substituents such as halogen or hydroxy groups which will not appreciably interfere with the hydrophobicity and $R_3$ is an alkyl group having 1–18 carbon atoms. Examples of such compounds are 2-(N-decyl-N,N-dimethyl amino)acetate, 2-(N-coco-N,N-dimethyl amino)acetate, 2-(N-cetyl-N,N-dimethyl amino)acetate, 2-(N-stearyl-N,N-dimethyl amino)acetate and C-hexadecyl-N,N,N-trimethyl betaine, etc. These above named compounds and other which conform to general structure III supra, are alkylated amino derivatives such as inner salts of certain amino acids characterized by the presence of the zwitterion nucleus.

Such compounds may be commercially available and may also be synthesized by conventional methods such as reacting omega-halogenated long-chain fatty acids with tertiary amines or condensing a tertiary amine with a halogenated carboxylic ester and subsequently saponifying as described by Schwartz et al. in "Surface Active Agents" (1949), 220–223. Additional information concerning these compounds may be obtained by referring to U.S. Pat. Nos. 2,082,275, 2,203,009, 2,279,138 and, inter alia, Funderburk et al., U.S. Pat. No. 2.702,279.

Among the suitable long-chain substituted imidazolines are included those compounds corresponding to the following general structure;

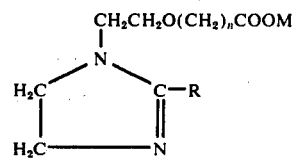

IV where n is from 3–9, M is a salt forming group such as an alkali metal, e.g., sodium, potassium, lithium, etc., and R is an alkyl radical having from 8–18 carbon atoms. Examples of such compounds are the sodium salt of 2-caprylic-1(ethyl-beta-oxipropanoic acid-)imidazoline, the sodium salt of 2-coconut-1(ethyl-beta-oxipropanoic)imidazoline.

Among the suitable N-alkyl beta aminopropionic acid type amphoteric detergents are included N-coco beta amino propionic acid and the sodium salt of said acid, the disodium salt of N-tallow beta amino propionate, the disodium salt or N-lauryl beta iminodipropionate, the partial sodium salt of N-lauryl beta aminodipropionate, N-lauryl myristyl-beta-amino propionic acid, and the triethylamino salt of N-lauryl myristyl-beta-amino propionic acid.

Suitable nonionic surfactants include the polyoxyalkylene alkyl ethers and the condensates of alkylene oxides with fatty acids. Suitable long chain amine oxides which are nonionic in basic solution and cationic in acid solution include dimethyl lauryl amine oxide, dimethyl cetyl amine oxide, dimethyl stearyl amine oxide, etc.; and the long chain cyclic amine oxides such as lauryl morpholine oxide and the like.

Suitable anionic surfactants include the higher fatty alcohol sulfates such as, for example, sodium lauryl sulfate; the alkylaryl sulfonates, e.g., sodium or potassium isopropylbenzene sulfonates, isopropyl naphthalene sulfonates; the alkali metal higher alkyl sulfosuccinates, e.g., sodium octenyl sulfosuccinate, sodium N-methyl-N-palmitoyl taurate, sodium oleyl isothionate; the alkali metal salts of alkylarylpolyethoxyethanol sulfates or sulfonates, e.g., the sodium t-octylphenoxypolyethoxyethyl sulfates and sulfonates having from 1 to 5 oxyethylene units.

Aside from the various types of anionic, synthetic detergents mentioned above, the laurylsulfoacetamide type, sulfated fatty acyl monoethanolamide, sodium sterate, and the sodium salts of the long chain ($C_8$-$C_{18}$) acyl-sarcosinates made by condensing a fatty acid chloride with N-methyl glycine, are also useful in the practice of this invention.

Suitable cationic surfactants include the cetyltrimethyl ammonium salts and the corresponding coconut fatty and octadecyl analogues, the higher alkyl dimethylmethallylammonium halides wherein said alkyl groups have from 8 to 18 carbon atoms, e.g., octyl, decyl, dodecyl, or octadecyl, t-octylphenoxyethoxyethoxydimethylbenzylammonium chloride, the dialkylguanidines and biquanidines, wherein the alkyl groups contain from 8–20 carbon atoms, cetyl dimethyl amine acetate, lauryl piperidinium chloride, the 2-alkyl-tetrahydroindoles, etc.

With regard to proportions, the final hair conditioning shampoo compositions herein essentially contain from 0.1 to 10.0%, by weight, of the total solution of the cationic polymer and from 1 to 25%, by weight, of the total solution of the amphoteric detergent, and from 0 to 20%, by weight, of the total solution of at least one nonionic surfactant or at least one ionic surfactant or a combination thereof, wherein any plurality of ionic surfactants used consists of those of the same ionogenic class only.

The practitioner will recognize that the actual concentration of any particular cationic polymer used in a given conditioning shampoo preparation encompassed within this invention may vary within the prescribed range, for many reasons. For example, the maximum usable concentration will depend on the nature and molecular weight of the polymer, its compatibility with the particular amphoteric detergent and any optional ingredients used, the degree of pH adjustment, if required, and the neutralizing agent utilized.

In the practice of this invention, it is preferred that the resin depositing, cationic polymer used be the phosphate salt of one of the following: poly(aminoethyl acrylate) or poly(aminoethyl hydroxypropyl acrylate) or a terpolymer of an aminoalkyl ester of an ethylenically unsaturated carboxylic acid, an amide of an ethylenically unsaturated carboxylic acid, and a hydroxyalkyl ester of an ethylenically unsaturated carboxylic acid wherein said cationic polymer has a molecular weight between about 25,000 and 100,000 and is used at a concentration ranging from about 0.5 to about 3.0 percent, by weight, of the total solution; that the amphoteric detergent used be lauric imidazoline dicarboxylate sodium salt such as represented in structure II hereinabove wherein R is $C_{11}H_{23}$ M is sodium, and $R_1$ is ethylene, at a concentration of from 1 to 25 percent, by weight, of the total solution; and that from 0 to 25 percent, by weight of the total solution, of s surfactant selected from the group consisting of: sodium lauryl sulfate, sodium lauryl ether sulfate, polyoxyethylene (4 moles) lauryl ether, dimethyl lauryl amine oxide or a combination thereof be used, as described hereinabove.

Since some of the ingredients employed in the practice of this invention tend to support bacterial growth, a small amount of a preservative should be added to prevent such microbial growth. Though other well known preservatives and bactericides such as formaldehyde may be employed, we prefer to use the lower molecular weight alkyl p-hydroxybenzoates.

Optional ingredients, in addition to the nonionic and ionic surfactants described hereinabove, may be incorporated into the conditioning shampoo compositions of this invention in order to modify certain properties thereof. Among these additives may be included: emollients and lubricants such as glycols, esters, and glycerine; lanolin compounds; protein hydrolyzates and other protein derivatives, ethylene oxide adducts, and cholesterol derivatives; dyes and other colorants, perfumes, and ultraviolet light absorbers, chelating agents and foam boosters. The polymeric conditioning agents show little or no tendency to react with such additives.

The resulting shampoo formulations exhibit all of the characteristics required of such products. They are capable of thoroughly cleaning the hair and depositing thereon a film which is transparent, glossy, flexible, and strong.

The films deposited on the hair fibers, by the present, novel shampoo compositions, possess good antistatic properties, adhere well to the hair, allow the hair to be readily recombed, do not become tacky when exposed to high humidities and are easily removed by conventional shampoos. In addition, it should be noted that the conditioning shampoos of this invention remain effective in cleaning the hair and imparting the desired manageability, wet and dry combing and, at times, curl retention properties thereto, when optional, conventional ingredients are incorporated therein.

The combined hair cleaning and conditioning procedure used in practicing this invention is essentially the same as that of a conventional shampoo technique. Ordinarily the hair is wetted; the shampoo preparation, as a concentrate, is applied and thoroughly massaged throughout the hair to ensure even distribution of the lather thus produced; the hair is then rinsed free of the lather, wiped partially dry, combed, and fixed in the desired configuration in which it is allowed to dry. The dried hair is then combed out into the desired set. Obviously, the practitioner may elect to repeat the cycle or otherwise vary from this technique without departing from the scope of this invention.

The invention will now be further illustrated by, but not intended to be limited by, the following examples. The quantities of all ingredients are given in parts, by weight, of the total formulation, unless specified otherwise.

EXAMPLE I

This example illustrates the preparation and effectiveness of a shampoo composition, using a salt of an aminoalkyl ester of a homopolymer of an ethylenically unsaturated carboxylic acid in combination with an amphoteric detergent and a polar nonionic surfactant, in accordance with this invention.

In this instance, said polymer was the phosphate salt of poly(aminoethyl acrylate) prepared by the method taught in Example I of assignee's U.S. Pat. No. 3,372,149, using phosphoric acid in lieu of hydrochloric acid. The amphoteric detergent was a dicarboxylic coconut oil derivative, and the polar nonionic surfactant was a long chain amine oxide. The shampoo formulation was as follows:

| Ingredient | Amount |
| --- | --- |
| Phosphate salt of poly(aminoethyl acrylate) (19.2% aqueous solution) | 10.0 |
| Disodium salt of dicarboxylated coconut imidazoline (40% aqueous solution) | 20.0 |
| Dimethyl lauryl amine oxide (30% aqueous solution) | 5.0 |
| Deionized Water | 65.0 |

The above described ingredients were thoroughly mixed in a 150 milliliter beaker until a homogeneous solution was obtained. The resulting solution was then tested for its ability to shampoo and condition hair by the following method.

Approximately one gram of the above described shampoo formulation was uniformly applied to each of three wet swatches of European hair, each 10 inches in length and weighing approximately 2 grams. Each of the shampoo bearing swatches was gently massaged for about two minutes, whereupon a lather was produced. The lather was then rinsed from the hair with warm tap water for one minute. The foregoing steps were then repeated. Excess water was then squeezed out of the thoroughly rinsed swatches by running them between two fingers. The swatches were combed and dried in an oven at 140° F.

It was observed during the washing cycle, that the shampoo composition exhibited good lathering. More importantly, it was observed that the hair was in excellent condition, e.g., combable lustrous, and manageable, due to the outstanding conditioning properties imparted to the shampoo composition by the cationic polymer.

EXAMPLE II

This example illustrates the ability of a shampoo composition prepared in accordance with this invention, to deposit a resin on the hair. The resin depositing ability of the test compositions herein was evaluated on the basis of a "Dye Acceptance Test" wherein the observed amounts of an anionic dye retained by hair shampooed with said compositions were compared to the amounts retained by hair shampooed with controls without cationic polymers. The test procedure is described hereinbelow.

In this example, a shampoo composition having the same formulation as that disclosed in Example I was tested along with another test sample having the same formulation, except the dimethyl lauryl amine oxide had been omitted, and four controls of which three were based on varied omissions of the former test sample.

The test sample compositions and those of the three special controls were prepared, spearately, in designated 150 milliliter beakers. The respective formulations for these compositions were as follows:

| Ingredient | Test Samples | | Control Nos. | | |
|---|---|---|---|---|---|
| | I | II | I | II | III |
| Poly(aminoethyl acrylate phosphate) (19.2% aqueous solution) | 10.0 | 10.0 | — | — | — |
| Dicarboxylic coconut imidazoline disodium salt (40% aqueous solution) | 20.0 | 20.0 | 20.0 | 20.0 | — |
| Dimethyl lauryl amine oxide (30% aqueous solution) | 5.0 | — | — | 5.0 | 5.0 |
| Distilled water | 65.0 | 70.0 | 80.0 | 75.0 | 95.0 |

The resulting solutions of the above described preparations and an additional control consisting of a commercial anionic shampoo concentrate were tested for their ability to deposit a conditioning film on 2 gram, 10 inch long swatches of bleached blond hair by means of the aforementioned "Dye Acceptance Test" as follows:

A sufficient number of the swatches of hair were first rinsed with warm water and then each shampooed with the test sample or a particular control by the same manner utilized in Example I, except herein the lather was allowed to remain on the hair for about five minutes during each cycle. Upon being dried by the prescribed method, each swatch was soaked for 15 minutes in 25 milliliters of an aqueous Orange II dye solution contained in a 100 milliliter beaker. Said dye solution comprised 0.6 grams of the dye in 1 liter of distilled water. Thereafter the swatches were removed from the dye solution rinsed for 1 minute with warm water, and dried in an oven set at 150° F. Conclusions based on subjective evaluations of the dye remaining on the hair were then made.

It was observed that though all of the swatches were orange to some varying degree, those shampooed with the test samples, having a cationic polymer therein, were most intense. It was concluded that the cationic polymer had been deposited on the hair by the shampoo.

EXAMPLE III

This example illustrates the preparation of and the effectiveness of a shampoo composition, using a cationic terpolymer of an amide of an ethylenically unsaturated carboxylic acid, a hydroxyalkyl ester of an ethylenically unsaturated carboxylic acid, and an amino alkyl ester of an ethylenically unsaturated carboxylic acid; in combination with an amphoteric detergent and an anionic surfactant, in accordance with this invention.

In this instance, the terpolymer base was obtained by conventional polymerization, and the phosphate salt of the aminoalkyl ester thereof was prepared by the method taught in Example I of assignee's U. S. Pat. No. 3,372,149, using phosphoric acid in lieu of hydrochloric acid. The resulting cationic terpolymer comprised 15 mole per cent of acrylamide, 10 mole percent of hydroxypropylacrylate, and 75 mole per cent of aminoethylacrylate phosphate. The amphoteric detergent was a disodium salt of a dicarboxylic lauryl imidazoline, and the anionic surfactant was a sodium salt of a sulfated ethoxylated, long chain alkyl alcohol. In addition to the foregoing ingredients, various optional ingredients were incorporated in the present shampoo composition. The latter ingredients were mixed with the anionic surfactant and then admixed with the cationic terpolymer and the amphoteric detergent as set forth in the following formulation:

| | Ingredients | Amount |
|---|---|---|
| Part I | Phosphate salt of a terpolymer of acrylamide, hydroxypropylacrylate, and aminoethyl acrylate (14% aqueous solution) | 14.30 |
| | Dicarboxylic lauryl imidazoline disodium salt (40% aqueous solution) | 10.00 |
| | Deionized water | 69.25 |
| Part II | Propylene glycol | 0.25 |
| | Polyoxyethylene (4 moles) lauryl ether | 1.00 |
| | Sodium lauryl ether sulfate (28% aqueous solution) | 5.00 |
| Part III | Methyl p-hydroxy benzoate | 0.10 |
| | F. D. and C. Red Dye No. 2 (2% solution) | 0.05 |
| | Water soluble perfume | 0.05 |

The ingredients of Part I were thoroughly mixed in a 150 milliliter beaker. Then the slightly agitated ingredients of Parts II and III were added to said beaker, and the mixture was stirred until it became a homogeneous solution. When this formulation was tested according to the manner set forth in Example I, supra, it exhibited very good lathering capability and imparted excellent wet and dry combing properties to the hair. Furthermore, when several wet combed hair swatches shampooed with the test sample and control swatches shampooed with a commercial shampoo were curled around a mandrel (½ inch diameter) and air dried over a period of from 3–4 hours. the curled swatches shampooed with the test sample retained more of the curl configuration.

EXAMPLE IV–V

Example III was repeated twice, except the concentration of the copolymer solution, in one case, was increased to 28.60 parts and to 42.90 parts, in the other. Accordingly the concentrations of the water were decreased to 54.95 parts and 40.65 parts, respectively. When tested in the above described manner, these shampoo compositions yielded conditioning and setting properties which were slightly improved over those obtained in Example I.

EXAMPLE VI

This example Illustrates the usefulness of a cationic copolymer of an ethylenically unsaturated carboxylic acid and a hydroxyalkyl ester of an ethylenically unsaturated carboxylic acid, in combination with an amphoteric surfactant and an anionic surfactant, at varied pH levels, in accordance with this invention.

To make the phosphate salt of a copolymer of the aminoalkyl ester acrylic acid and hydroxypropyl acrylate employed in the present series of shampoo compositions, the method taught in Example I of assignee's U.S. Pat. No. 3,372,149 was utilized with phosphoric acid instead of hydrochloric acid. The copolymer was prepared using 75% mole percent of acrylic acid and 25 mole percent hydroxypropyl acrylate. The amphoteric detergent used was a cocoamido betaine, and the anionic surfactant used was a sodium salt of a sulfated ethoxylated lauryl alcohol. In addition to the foregoing essential ingredients, various optional additives were incorporated in the present shampoo composition as set forth in the following formulations:

In each of the above described preparations, the ingredients of Part I were thoroughly mixed in a 150 milliliter beaker. Then the ingredients of Part II were added separately to said beaker, and moderate stirring was continued until a homogeneous solution was obtained.

Portions of the above described formulations were then tested and evaluated for their effectiveness as conditioning shampoo compositions by the methods utilized in Example I hereinabove. During the wash cycles, it was observed that each sample displayed an outstanding ability to produce a thick lather. Test results are presented below.

| Material Tested | Wet Combing | Condition of Dried Hair |
| --- | --- | --- |
| Sample A | Excellent | Very stiff |
| Sample B | Very good | Stiff |
| Sample C | Very good | Stiff |

As indicated by the data above, shampooing performances wherein the pH levels were lower were superior.

EXAMPLE VII

This example illustrates the usefulness of a cationic copolymer of an ethylenically unsaturated carboxylic acid and a hydroxyalkyl ester of an ethylencally unsaturated carboxylic acid, in combination with an amphoteric detergent, one anionic surfactant, and one nonionic surfactant, in accordance with this invention.

A phosphate salt of a copolymer of an amionalkyl ester of acrylic acid and hydroxypropyl acrylate as in Ex. VI was employed, at varied concentrations, in a series of three shampoo formulations having fixed amounts of a cocoamido betaine, a sodium salt of a sulfated ethoxylated lauryl alcohol, and a highly concentrated alkanolamide. In addition to these essential ingredients, various optional additives were incorporated in the present shampoo compositions as set forth below.

| Part I | Ingredients | Sample Iden. and Amount | | |
| --- | --- | --- | --- | --- |
| | | A | B | C |
| | Phosphate salt of poly(aminoethyl acrylate hydroxypropyl acrylate) (18% aqueous solution) | 30.0 | 30.0 | 30.0 |
| | Cocoamido betaine (32% aqueous solution) | 20.0 | 20.0 | 20.0 |
| | Deionized water | 39.8 | 39.8 | 39.0 |
| Part II | | | | |
| | Methyl p-hydroxy benzoate | 0.1 | 0.1 | 0.1 |
| | Sodium lauryl ether sulfate (28% solution) | 10.0 | 10.0 | 10.0 |
| | F. D. and C. Red Dye No. 2 (2% solution) | 0.05 | 0.05 | 0.05 |
| | Water soluble perfume | 0.05 | 0.05 | 0.05 |
| | Aqueous sodium hydroxide solution (10%) added to yield a pH of | 3.50 | 5.00 | 7.00 |

| Part I | Ingredients | Sample Identification and Amount | |
| --- | --- | --- | --- |
| | | D | E |
| | Phosphate salt of poly-(aminoethyl acrylate hydroxypropyl acrylate) (18% aqueous solution) | 20.0 | 30.0 |
| | Fatty amidoalkyl betaine | 15.0 | 20.0 |

-continued

| Part I | Ingredients | Sample Identification and Amount | |
|---|---|---|---|
| | | D | E |
| | (30% aqueous solution) | | |
| | Distilled water | 57.80 | 42.80 |
| Part II | | | |
| | Sodium lauryl ether sulfate (28% aqueous solution) | 5.00 | 5.00 |
| Part III | | | |
| | Lauric diethanolamide (90% active) | 2.00 | 2.00 |
| Part IV | | | |
| | Methyl p-hydroxy benzoate | 0.10 | 0.10 |
| | F. D. and C. Red Dye No. 2 (2% solution) | 0.05 | 0.05 |
| | Water soluble perfume | 0.05 | 0.05 |

In each of the above described preparations, the ingredients in Parts I and II were thoroughly mixed in their respective containers. Then Part II was added to Part I, and the resulting mixture was stirred until it became homogeneous. This mixture was then heated to an maintained at 50° C., while the melted Part III was added thereto. Then this smooth mixture was cooled to about 23° C., and Part IV was added, as moderate stirring was continued.

Portions of the above described formulations were then tested and evaluated for their effectiveness as conditioning shampoo compositions by the method utilized in Example I hereinabove. Tests compared as follows:

| Material Tested | Compatibility | Ability to Produce Lather | Wet Combability | Condition of Dried Hair |
|---|---|---|---|---|
| D | Excellent | Good | Excellent | Stiff |
| E | Excellent | Good | Excellent | Stiff |

The data summarized above clearly indicates the ability of a cationic copolymer to impart the desired conditioning properties, when employed in combination with a betaine type detergent, an anionic surfactant, and a nonionic surfactant in a shampoo composition, in accordance with this invention.

EXAMPLE VIII

This example further illustrates the usefulness of shampoo compositions having, in addition to a cationic copolymer, an amphoteric detergent in combination with a nonionic surfactant, in accordance with this invention.

In this instance the cationic copolymer was the nitrate salt of a copolymer of the aminoalkyl ester of acrylic acid and hydroxypropyl acrylate prepared by the method taught in Example I of assignee's U.S. Pat. No. 3,372,149, using nitric acid in lieu of hydrochloric. The copolymer contained 75% acrylic acid and 25% hydroxypropyl acrylate. The amphoteric detergent was the disodium salt of a dicarboxylic lauryl detergent was the disodium salt of a dicarboxylic lauryl imidazoline. the anionic surfactant was the sodium salt of a sulfated ethoxylated lauryl alcohol and the nonionic surfactant was an ethylene oxide - lauryl alcohol condensate. In addition, various optional additives were incorporated in the present shampoo composition as set forth in the following formulations:

| Part I | Ingredients | Amount | | |
|---|---|---|---|---|
| | | F | G | H |
| | Nitrate salt of poly(aminoethyl acrylate hydroxypropyl acrylate) (18% aqueous solution) | 10.00 | 20.00 | 30.00 |
| | Dicarboxylic lauric imidazoline disodium salt (40% aqueous solution) | 10.0 | 15.00 | 20.00 |
| | Deionized water | 73.55 | 58.55 | 43.55 |
| Part II | | | | |
| | Propylene glycol | 0.25 | 0.25 | 0.25 |
| | Polyoxyethylene (4 moles) lauryl ether | 1.00 | 1.00 | 1.00 |
| | Sodium lauryl ether sulfate (28% aqueous solution) | 5.00 | 5.00 | 5.00 |
| | Methyl p-hydroxy benzoate | 0.10 | 0.10 | 0.10 |
| | F. D. and C. Red Dye No. 2 (2% aqueous solution) | 0.05 | 0.05 | 0.05 |
| | Water soluble perfume | 0.05 | 0.05 | 0.05 |

The ingredients of Part I were throughly mixed in a 150 milliliter beaker. Then the slightly agitated ingredients of Part II were added to said beaker and the mixture was stirred until a homogeneous solution was obtained.

When 0.50 gram samples of the present shampoo compositions were used to wash 2 gram, 10 inch swatches of hair in the manner employed in Example I, it was observed that a thick lather was produced in each case, and each composition yielded very good wet combability and conditioning properties.

EXAMPLE IX

This example still further illustrates the usefulness of a shampoo composition having, in addition to a cationic copolymer, a particular amphoteric detergent in combination with an anionic surfactant and a nonionic surfactant, in accordance with this invention.

To make the present shampoo composition, the method of preparation outlined in Example I was repreated, using the following ingredients in their respective amounts:

| Ingredient | Amount |
| --- | --- |
| Phosphate salt of poly(aminoethyl acrylate hydroxypropyl acrylate) (18% aqueous solution) (as used in Example VI) | 10.00 |
| The triethanolamine salt of N-lauryl myristyl-beta-amino propionic acid (50% aqueous solution) | 10.0 |
| Deionized water | 68.0 |
| Sodium lauryl ether sulfate (28% aqueous solution) | 10.0 |
| Lauric diethanolamide (conc.) | 2.0 |

When samples of the above described formulations were used to wash swatches of hair in the manner set forth in Example I hereinabove, it was observed that thick lathers were produced in each case. Furthermore, the present composition displayed excellent conditioning properties.

EXAMPLE X

This example illustrates the effectiveness of incorporating a second nonionic surfactant into a shampoo formulation having, in addition to a cationic copolymer and an amphoteric surfactant, an anionic surfactant in combination with a nonionic surfactant, in accordance with this invention.

In this case, 1 part of a high purity fatty acid alkanolamide was added to 99 parts of each of three shampoo compositions having formulations as described in Example VIII hereinabove. The alkanolamide additions were made in the manner set forth in Example VII, supra.

Upon treating 2 gram swatches of hair with 0.25 gram samples of the above described shampoo compositions in the manner set forth in Example VIII hereinabove, it was observed that foamability was significantly improved over those exhibited by the shampoo compositions prepared in Example VIII. Each composition yielded very good wet combability and conditioning properties.

EXAMPLE XI

This example illustrates the unusual curl retention properties of a cationic polymer based shampoo typical of this invention.

To make the present shampoo composition, a cationic copolymer similar to that described in Example VI hereinabove was employed with a particular amphoteric detergent in combination with a cationic surfactant and various optional ingredients. A control sample, wherein the cationic copolymer had been omitted, was also prepared. The respective test sample and control formulations were as follows:

| Ingredient | Test Sample | Control |
| --- | --- | --- |
| Phosphate salt of poly(aminoethyl acrylate-hydroxypropyl acrylate) (18% aqueous solution) (as in Ex. VI) | 10.0 | — |
| Dicarboxylic coconut imidazoline sodium salt (40% aqueous solution) | 20.0 | 20.0 |
| Dimethyl laurylamine oxide | 5.0 | 5.0 |
| Distilled water | 64.8 | 74.8 |
| F. D. and C. Red Dye No. 2 (2% solution) | 0.05 | 0.05 |
| Water soluble perfume | 0.05 | 0.05 |
| Methyl p-hydroxy benzoate | 0.10 | 0.10 |

The above described formulations were mixed in separate 150 milliliter beakers. In each case, a clear homogeneous solution was obtained. Portions of the resulting solutions were then used to wash swatches of bleached European hair, in the manner described in Example I hereinabove, and subsequently tested for their conditioning and curl retention properties as set forth below. Step I - Each of the wet swatches resulting from the washing was combed to eliminate any tangling. Observations of any tendency to tangle or snarl were recorded. Each of the shampoo formulations which was tested was rated as poor or fair or excellent with respect to its wet combing properties. The wet combed swatches were next wound on separate polytetrafluoroethylene mandrels; each of said mandrels having a one-half inch diameter. Then each curl was removed from the mandrel and secured with a clip. Each of the thus formed curls was dried at 140° F. for about 30 minutes and then conditioned overnight at 72° F. and a relative humidity of 50 percent. Step 2 - After the conditioning period was completed, the clips were removed, and the curls were unwound into helical configurations. In each case, the curl was measured for initial length (L) by placing said configurations onto a graduated, plexiglas retention board. Then the curls were placed in a cabinet wherein the temperature was maintained at 72° F. and the relative humidity at 90 percent. The length of each curl was recorded initially after 10 minutes, and thereafter at 30 minute intervals over a period of 120 minutes. The following formula was used to calculate the percent curl retention:

$$\text{Per Cent Curl Retention} = \frac{(L - L_t)}{(L - L_o)} \times 100,$$

wherein L = length of the fully extended hair,
$L_o$ = length of curl before exposure to 90 percent relative humidity,
$L_t$ = length of curl (at time t) after exposure to 90 percent relative humidity.

Conclusions based on observations throughout the testing and mean percent curl retention results from 9 replicate determinations are compared in Table No. 1.

Table No. 1

| Material Tested | Wet Combability | Condition of Dried Hair | Mean % Curl Retention Exposure Time (minutes) | | | | | |
|---|---|---|---|---|---|---|---|---|
| | | | 10 | 20 | 30 | 60 | 90 | 120 |
| Test Sample | Excellent | Stiff | 80.2 | 61.9 | 55.4 | 44.6 | 40.2 | 37. |
| Control | Fair | Soft | 69.4 | 47.0 | 37.0 | 25.4 | 20.7 | 19. |

As indicated by the data summarized above, the curl retention properties, as well as the general conditioning properties, of the test formulation were superior to those of the control.

EXAMPLE XII

This example illustrates the effectiveness of shampoo compositions, in accordance with this invention, having increased amounts of the amphoteric surfactant and a particular anionic surfactant.

Two shampoo compositions, I and J, comprising aqueous solutions of a cationic copolymer similar to that employed in Example VI hereinabove, a dicarboxylic coconut imidazoline derivative, and a sodium salt of a sulfated ethoxylated alkyl sulfate were prepared as follows:

Part I — The following ingredients were thoroughly mixed in two respectively designated 150 milliliter beakers:

| Ingredient | Sample Iden. and Amount | |
|---|---|---|
| | I | J |
| Phosphate salt of poly(aminoethyl acrylate hydroxypropyl acrylate) (18% aqueous solution)(as in Ex. VI) | 15.0 | 20.0 |
| Dicarboxylic coconut imidazoline disodium salt (40% aqueous solution) | 25.0 | 25.0 |
| Distilled water | 39.0 | 39.0 |
| Hydrochloric acid (conc.) | 1.0 | 1.0 |

Part II – formulation I above, there were added 20.0 parts of sodium lauryl ether sulfate, and to formulation J there were added 15.0 parts of the same anionic surfactant. Thereafter stirring was continued until solutions were obtained.

The above described solutions were then tested for their curl retention properties by the method utilized in Example X hereinabove using a 1 gram application of each shampoo composition per 2 grams of hair. During the testing, it was observes that both of the present sample formulations produced very thick lathers. Other pertinent observations and means curl retention results are presented in Table No. 2.

Table No. 2

| Material Tested | Wet Combability | Conditions of Dried Hair | Mean % Curl Retention | |
|---|---|---|---|---|
| | | | 30 min. | 120 min |
| Sample I | Excellent | Stiff | 48.2 | 35.7 |
| Sample J | Excellent | Stiff | 55.2 | 43.2 |

As indicated by the data summarized above, the curl retention properties, as well as the general conditioning properties, of the test sample were superior to those of the control.

EXAMPLE XIII

This example illustrates the usefulness of shampoo compositions having, in addition to a cationic polymer and an amphoteric detergent at varied concentrations, an anionic surfactant in combination with a nonionic surfactant, in accordance with this invention.

To make a series of three shampoo compositions, the procedural steps of Example VIII were repeated, using the phosphate salt of poly(aminoethyl-acrylate-hydroxypropyl acrylate) (prepared as in Example VI) instead of the nitrate salt.

When samples of the above described formulations were used to wash 4 gram, 10 inch swatches of hair in the manner set forth in Example I, it was observed that a thick layer was produced in each case. More importantly, these compositions yielded excellent washings and conditioning properties.

EXAMPLE XIV

This example illustrates the usefulness of a cationic copolymer of an aminoalkyl ester of an ethylenically unsaturated carboxylic acid and a hydroxyalkyl ester of an ethylenically unsaturated carboxylic acid, in combination with an amphoteric detergent, a nonionic surfactant, and an anionic surfactant, in accordance with this invention. Said cationic copolymer and said amphoteric detergent were employed at varied concentrations.

To make the phosphate salt of the copolymer of aminoalkyl ester of acrylic acid and hydroxylpropyl acrylate employed in the present series of shampoo compositions, K, L, and M, the method taught in Example I of assignee's U.S. Pat. No. 3,372,149 was utilized with the phosphoric acid salt instead of that of hydrochloric acid. The amphoteric detergent was the sodium salt of a dicarboxylic lauric imidazoline derivative; the nonionic surfactant was an ethylene oxide condensate of lauryl alcohol; and the anionic surfactant, a sodium salt of a sulfated ethoxylated long-chained alcohol sulfate. In addition to the foregoing essential ingredients, optional additives were incorporated, in each of three shampoo formulations as set forth below.

| Part I | Ingredients | Sample Iden. and Amount | | |
|---|---|---|---|---|
| | | K | L | M |
| | Phosphate salt of poly(aminoethyl acrylate hydroxypropyl acrylate) (18% aqueous solution) (of Ex. VI) | 10.00 | 20.00 | 30.00 |
| | Dicarboxylic lauric imidazoline disodium salt (40% aqueous solution) | 10.00 | 15.00 | 20.00 |
| | Distilled water | 73.55 | 58.55 | 43.55 |
| Part II | Propylene glycol | 0.25 | 0.25 | 0.25 |
| | Polyoxyethylene (4 moles) lauryl ether | 1.00 | 1.00 | 1.00 |
| | Sodium lauryl ether sulfate (28% aqueous solution) | 5.00 | 5.00 | 5.00 |
| | Methyl p-hydroxy benzoate | 0.10 | 0.10 | 0.10 |
| | F. D. and C. Red Dye No. 2 (2% solution) | 0.05 | 0.05 | 0.05 |
| | Water soluble perfume | 0.05 | 0.05 | 0.05 |

In each of the above described preparations, the ingredients of Part I were thoroughly mixed in a 150 milliliter beaker. Then the ingredients of Part II were added to said beaker, and stirring was continued until a homogeneous solution formed. Thereafter, the pH level of each sample was adjusted to about 5.0 by the addition of dilute hydrochloric acid.

It was observed that upon diluting 1 part of each sample composition with 50 parts of water, precipitation occurred in all cases.

Portions of the above described formulations were then tested and evaluated for their effectiveness as conditioning shampoo compositions by the methods utilized in Example I hereinabove. During the wash cycles, it was observed that lathering, in each case, was very good. Test results compared as follows in Table No. 3.

Table No. 3

| Material Tested | Wet Combing | Condition of Dried Hair |
|---|---|---|
| Sample K | Excellent | Stiff |
| Sample L | Excellent | Stiff |
| Sample M | Excellent | Stiff |

The data summarized above indicates that a shampoo composition employing an ionic surfactant and nonionic surfactant combination in accordance with this invention, is also effective.

EXAMPLE XV

This example illustrates the ability of the shampoo compositions of this invention to improve the condition of the hair, when employed in commercial, salon hair-setting operations.

In this case, two series of comparative tests were conducted by professional hairdressers, using, in each instance, a novel shampoo composition on one side of the head of an individual and a standard control on the other side. The particular novel shampoo compositions used were those respectively having the same formulations as samples L and M of Example XIV, and said standard controls had the same formulation without the cationic copolymer. Each test was run, successively, on the hair of eight individuals as follows:

The hair was first combed and evenly parted. Then the left side was secured with hairpins, and the right side of hair was wetted with warm water. Thereafter one teaspoonful of the particular test shampoo was gently massaged into the wetted hair. Massaging was continued for about 2 minutes to assure uniform distribution of the resulting lather, throughout the wet air. Then the lather was rinsed from the hair by means of a warm water spray accompanied with gentle massaging. The shampooing steps were repeated, and the hair was rinsed thoroughly, dried with a towel, and secured by hairpins.

Then the left side of the head was shampooed in the above described manner, using the standard control shampoo. After combing out these rinsed sides, the hair was then set in a similar configuration on both sides, with curlers, and dried under a conventional hair dryer. When the curlers were removed; and the hair combed out, comparisons of the left side with that of the right side of each individual were made based on objective evaluations by the professional hairdressers.

In each of the remaining tests, the hairdresser was not aware of which shampoo composition, whether test or control, was to be used on a particular side of the head. In fact, the identities of the shampoos were concealed by placing sufficient quantities of each test shampoo and of each of the corresponding controls in similar, numbered containers. Said containers were then separated into the two respective groups. Then the hairdresser was instructed to randomly select one container from each of said groups to shampoo either side of the head.

It was concluded that the test sample shampoos consistently yielded superior conditioning properties over the control shampoo, throughout the series. Furthermore, it became apparent that the shampoo compositions, prepared in accordance with this invention, are readily adaptable to professional use.

EXAMPLE XVI

This example illustrates the use of a cationic polymer, a sulfonated fatty amido-amphoteric detergent, and a nonionic surfactant in combination with three anionic surfactants, in the preparation of a shampoo composition in accordance with this invention.

A test sample consisting of an aqueous solution of a cationic copolymer such as that employed in Example VI hereinabove, the particular aforementioned essential surfactants, and various optional additives, and a control having an identical formulation, without the cationic copolymer, were prepared as follows:

Part I — The test sample and the control were prepared by first introducing the following ingredients into a separate, respectively designated 150 milliliter beaker:

| Ingredients | Sample Iden. and Amount | |
|---|---|---|
| | Test Sample | Control |
| Phosphate salt of poly(aminoethyl acrylate-hydroxypropyl acrylate) (18% aqueous solution) (prepared as in Ex. VI) | 10.0 | — |
| Sulfonated fatty amide (56% aqueous solution) | 10.0 | 10.0 |
| Water soluble protein hydrolysate | 1.5 | 1.5 |
| Distilled water | 52.8 | 62.8 |
| Methyl p-hydroxybenzoate | 0.1 | 0.1 |

Part II — The above described ingredients, in each case were stirred at 150° F. into a smooth, homogeneous mixture. Then, while stirring was continued at the said temperature, the following ingredients were added to each mixture:

| Ingredient | Amount |
|---|---|
| Sodium lauryl sulfate (30% aqueous solution) | 10.0 |
| Triethanolamine lauryl sulfate (45% aqueous solution) | 7.0 |
| Sodium N-methyl-N-"coconut oil acid" taurate (25% aqueous solution) | 6.0 |
| Lauric-myristic alkanolamide (90% active) | 2.5 |

Part III — As each of the preparations described in Part II, above became homogeneous, the temperature of the resulting solution was gradually decreased to 90° F. and there were added thereto 0.1 parts, by weight, of a water soluble perfume.

To test the effectiveness of the thusly prepared sample and control as conditioning shampoos, they were compared in a series of eight half head tests as described in Example XV. It was concluded that the test shampoo lathered well and consistently yielded superior conditioning properties over the control shampoo.

EXAMPLE XVII

This example illustrates a method for the preparation of a variety of shampoo formulations in accordance with the present invention. The polymers employed, the shampooing technique and testing methods employed are substantially as described in the preceding examples. In all cases, the amphoteric detergent is the lauric imidazoline dicarboxylate sodium salt present in the amount of 10% and sodium lauryl sulfate in an amount of 10% is used as surfactant. The cationic polymers (used at a concentration of 10%, by weight are as follows:

| | Polymers | Monomer proportions mole per cent |
|---|---|---|
| [A] | Hydrochloride salt of poly(aminoethyl acrylate/acrylamide) | 50/50 |
| [B] | Phosphate salt of poly(aminoethyl acrylate/aminoethyl crotonate) | 95/5 |
| [C] | Hydrochloride salt of poly(aminoethyl methacrylate | 100 |
| [D] | Phosphate salt of poly(2-aminopropyl acrylate/diethyl fumarate) | 75/25 |
| [E] | Phosphate salt of poly(aminoethyl acrylate/acrylamide/hydroxypropyl acrylate) | 80/4/16 |
| [F] | Phosphate salt of poly(aminoethyl acrylate/diethyl fumarate) | 85/15 |
| [G] | Phosphate salt of poly(aminoethyl maleate/vinyl methyl ether) | 50/50 |
| [H] | Phosphate salt of poly(N-ethyl aminoethyl methacrylate/dioctyl fumarate) | 80/20 |
| [I] | Sulfuric acid salt of poly(aminoethyl acrylate/monomethyl maleate) | 80/20 |
| [J] | Sulfuric acid salt of poly(N-methyl aminoethyl acrylate/ethyl acrylate) | 70/30 |
| [K] | Phosphate salt of poly(aminoethyl methacrylate/dodecyl methacrylate) | 80/20 |
| [L] | Hydrochloride salt of poly(aminoethyl acrylate/vinyl acetate) | 80/20 |

All the thus produced shampoos lather well and yield superior conditioning properties on the dried hair.

Summarizing, it is thus seen that this invention provides a novel preparation of a conditioning, hair shampoo. Moreover, this invention provides an efficient and economical composition which is useful in cleaning and conditioning human hair.

Variations may be made in the proportions, procedures, and materials without departing from the scope of this invention which is defined by the following claims.

We claim:

1. A shampoo composition comprising an aqueous solution of:
    A. from 0.1 to 10.0 percent, by weight, of the total solution of a water-soluble acid salt of an aminoalkyl ester of a cationic polymer having a molecular weight of 5,000 to 250,000 and selected from the group consisting of aminoalkyl esters of (a) a homopolymer of a homopolymerizable unsaturated carboxylic acid having 3 to 5 carbon atoms, (b) a copolymer of a copolymerizable mixture of unsaturated carboxylic acids having 3 to 5 carbon atoms, and (c) a copolymer of at least one of said acids having 3 to 5 carbon atoms and at least one copolymerizable ethylenically unsaturated comonomer selected from the group consisting of vinyl acetate, vinyl propionate, vinyl methyl ether, vinyl ethyl ether, the $C_1$-$C_{18}$ alkyl half esters of maleic and fumaric acids, amides of acrylic and methacrylic acids, and the $C_1$-$C_{18}$ alkyl and $C_2$-$C_4$ hyroxyalkyl esters of acrylic and methacrylic acids, wherein the copolymers of group (c) are prepared with at least 50 mole percent of the unsaturated carboxylic acid component, B. from 1 to 25 percent, by weight, of the total solution of an amphoteric detergent selected from the group consisting of
a. an imidazoline derivative corresponding to the formula

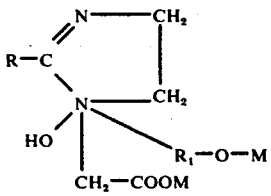

b. an imidazoline derivative corresponding to the formula

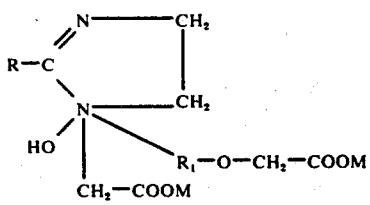

c. an imidazoline derivative corresponding to the formula

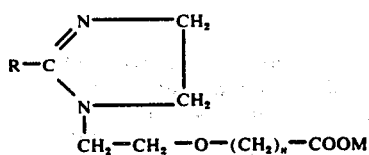

wherein R is an alkyl group having 8–18 carbon atoms, $R_1$ is a bivalent lower alkyl group having 2–4 carbon atoms, M is selected from the group consisting of alkali metals and hydrogen, and n is an integer from 3 to 9,
d. higher alkyl and higher alkyl amide betaines corresponding to the structure

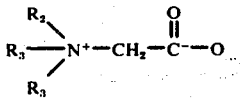

wherein $R_2$ is selected from the group consisting of $C_8$-$C_{18}$ alkyl groups, $C_8$-$C_{18}$ amido groups; $C_8$-$C_{18}$ alkyl groups substituted with ether or ester linkages or hydrogen substituted groups and $R_3$ is a $C_1$-$C_{18}$ alkyl group,
e. an N-alkyl-beta-aminopropionic acid wherein the alkyl group contains 8–18 carbon atoms,
f. $C_8$-$C_{18}$ amino sulfonates, and
g. the sulfonated alkyl amides wherein the alkyl groups contain 8 to 18 carbon atoms; and
C. from 0 to 20 percent, by weight of the total solution, of at least one surfactant selected from the group consisting of nonionic surfactants, ionic surfactants and combinations thereof other than amphoteric detergents of part B wherein any plurality of ionic surfactants utilized consists of those of the same ionogenic class.

2. The shampoo composition of claim 1 wherein said water-soluble acid salt of a cationic polymer is the phosphate salt of poly(aminomethyl acrylatehydroxypropyl acrylate).

3. The shampoo composition of claim 1 wherein said water-soluble acid salt of a cationic polymer is the phosphate salt of poly(aminoethyl acrylate).

4. The shampoo composition of claim 1 wherein part (A) is selected from the group consisting of the phosphate salt of poly(aminoethyl acrylate), the phosphate salt of poly(aminoethyl acrylate-ethyl acrylate), the phosphate salt of the aminoethyl ester of a terpolymer of acrylic acid, hydroxypropyl acrylate, and acrylamide, and the nitrate salt of poly(aminoethyl acrylate-hydroxypropyl acrylate, said part (A) being present at a concentration of from 2.0 – 6.0 percent, by weight, of the total solution.

5. The shampoo composition of claim 1 wherein part (C) is selected from the group consisting of dimethyl lauryl amine oxide, sodium lauryl ether sulfate, and polyoxyethylene (4 moles) lauryl ether.

* * * * *